United States Patent
Barlag

(10) Patent No.: US 8,920,727 B2
(45) Date of Patent: Dec. 30, 2014

(54) ARRANGEMENT AND METHOD FOR ELECTROCHEMICALLY MEASURING BIOCHEMICAL REACTIONS AND METHOD FOR PRODUCING THE ARRANGEMENT

(75) Inventor: Heike Barlag, Nürnberg (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

(21) Appl. No.: 13/138,345

(22) PCT Filed: Jan. 26, 2010

(86) PCT No.: PCT/EP2010/050842
§ 371 (c)(1),
(2), (4) Date: Aug. 4, 2011

(87) PCT Pub. No.: WO2010/089226
PCT Pub. Date: Aug. 12, 2010

(65) Prior Publication Data
US 2011/0286888 A1    Nov. 24, 2011

(30) Foreign Application Priority Data

Feb. 4, 2009   (DE) .......................... 10 2009 007 387
Sep. 28, 2009  (DE) .......................... 10 2009 043 228

(51) Int. Cl.
  *G01N 27/48*   (2006.01)
  *G01N 27/403*  (2006.01)
  *B01L 3/00*    (2006.01)

(52) U.S. Cl.
  CPC ....... *G01N 27/403* (2013.01); *B01L 2300/0825* (2013.01); *B01L 2300/0645* (2013.01); *B01L 2300/161* (2013.01); *B01L 3/502707* (2013.01); *B01L 2200/0689* (2013.01)
  USPC ...................................... 422/82.01; 204/409

(58) Field of Classification Search
  CPC ................ B01L 2200/0689; B01L 2300/0645; B01L 2300/0825; B01L 2300/161; B01L 3/502707; G01N 27/403
  USPC .............................. 204/409; 422/82.01–82.11
  See application file for complete search history.

(56) References Cited

U.S. PATENT DOCUMENTS 5,520,787 A      5/1996  Hanagan et al.
5,700,360 A  *  12/1997  Chan et al. .................... 205/778

(Continued)

FOREIGN PATENT DOCUMENTS

DE    102004020829     5/2006
DE    10 2006 038 271  2/2008

(Continued)

OTHER PUBLICATIONS

Szilveszter Gaspar et al., "Amperometric biosensor-based flow-through microdetector for microdialysis applications," Analytica Chimica Acta, Elsevier, vol. 525, No. 1, 2004, pp. 75-82.

(Continued)

*Primary Examiner* — J. Christopher Ball
(74) *Attorney, Agent, or Firm* — Roberts Mlotkowski Safran & Cole, P.C.; David S. Safran

(57) ABSTRACT

A device is intended to electrochemically measure biochemical reactions and includes a base plate, a sensor array situated on the latter, a coating of the base plate, and a sealing film with at least one recess. The recess is mechanically connected to the base plate and/or to the coating of the base plate and forms a flow cell above the sensor array. An inlet and an outlet of the flow cell are in the form of continuous recesses in the base plate. The active surfaces of the sensors are free of the coating and regions of the base plate adjacent to the sensors are covered by the coating.

18 Claims, 3 Drawing Sheets

(56) References Cited

U.S. PATENT DOCUMENTS

| | | |
|---|---|---|
| 7,367,221 B2 | 5/2008 | Hintsche |
| 2005/0268701 A1 | 12/2005 | Hintsche |
| 2009/0114293 A1 | 5/2009 | Kanai et al. |

FOREIGN PATENT DOCUMENTS

| | | |
|---|---|---|
| DE | 10 2006 053 474 | 5/2008 |
| DE | 10 2009 007 387 | 2/2009 |
| DE | 10 2009 043 228 | 9/2009 |
| EP | 1 591 780 | 11/2005 |
| EP | 1 950 569 | 7/2008 |
| EP | 2010/050842 | 1/2010 |
| WO | 2005/119200 | 12/2005 |

OTHER PUBLICATIONS

G. Jobst et al., "Mass producible miniaturized flow through a device with a biosensor array," Sensors and Actuators B Chemical, Elsevier, vol. 43, No. 1-3, 1997, pp. 121-125.

International Search Report for PCT/EP2010/050842, mailed on Apr. 13, 2010.

Chinese Office Action for related Chinese Patent Application No. 201080015573.1, issued May 28, 2013, 14 pages.

* cited by examiner

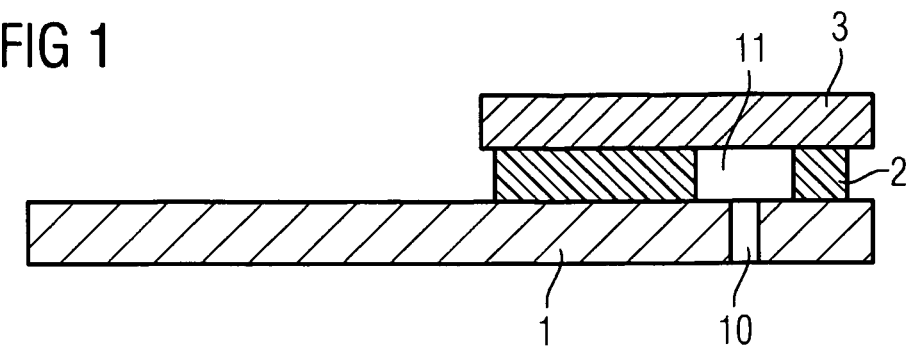
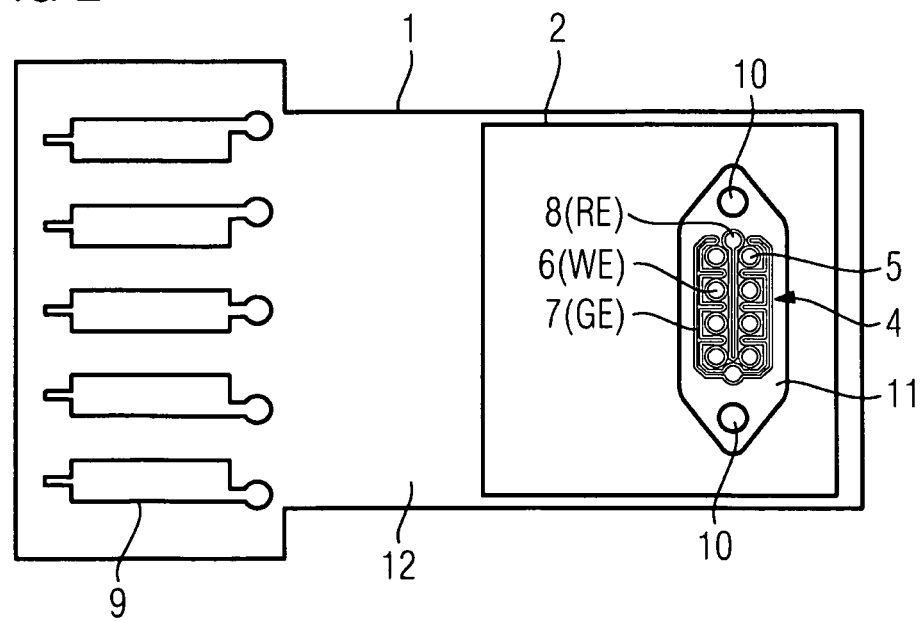

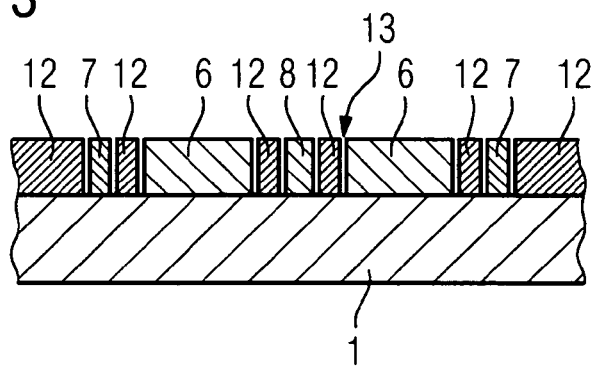
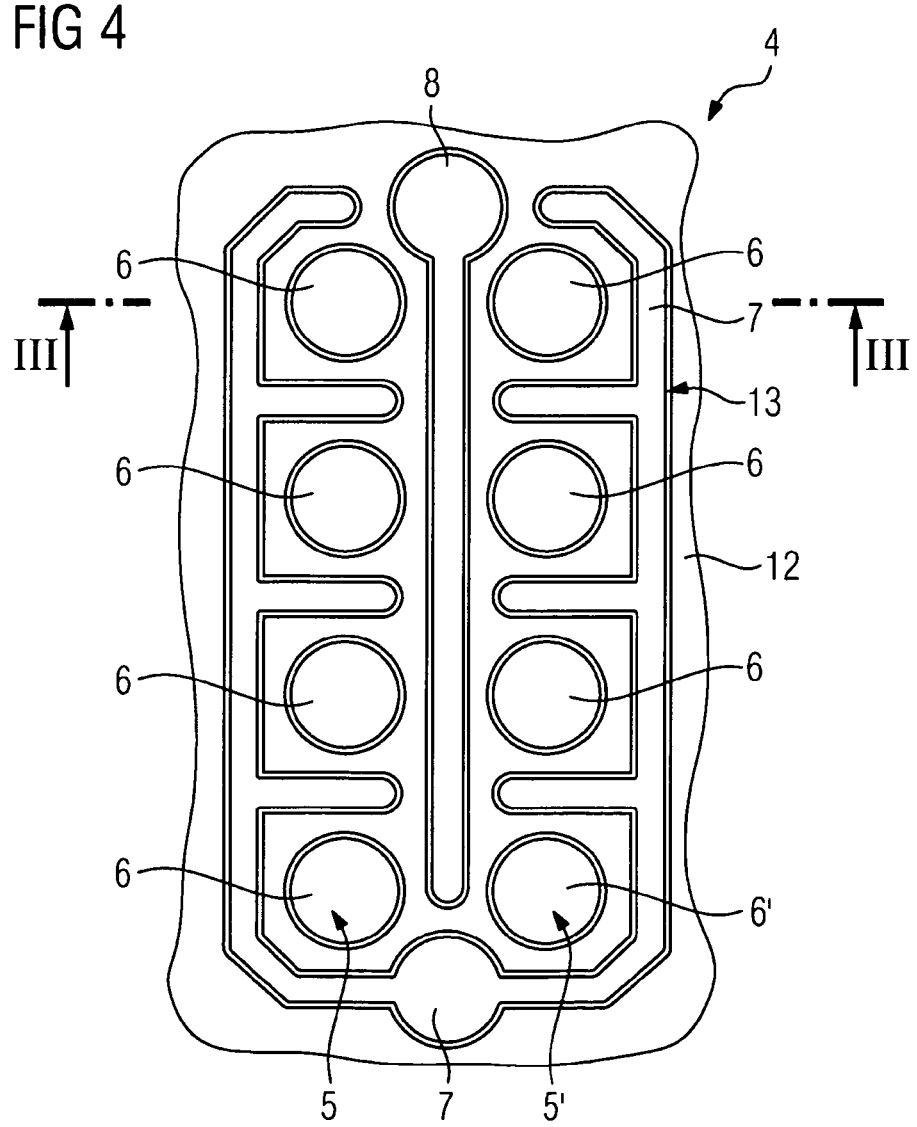

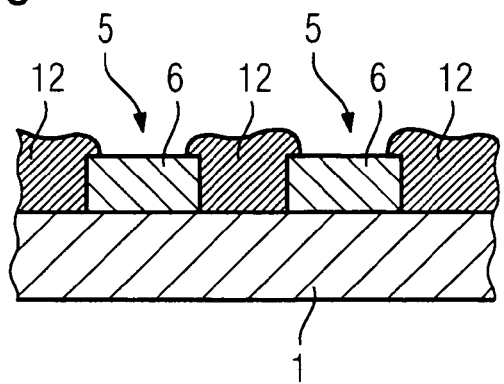
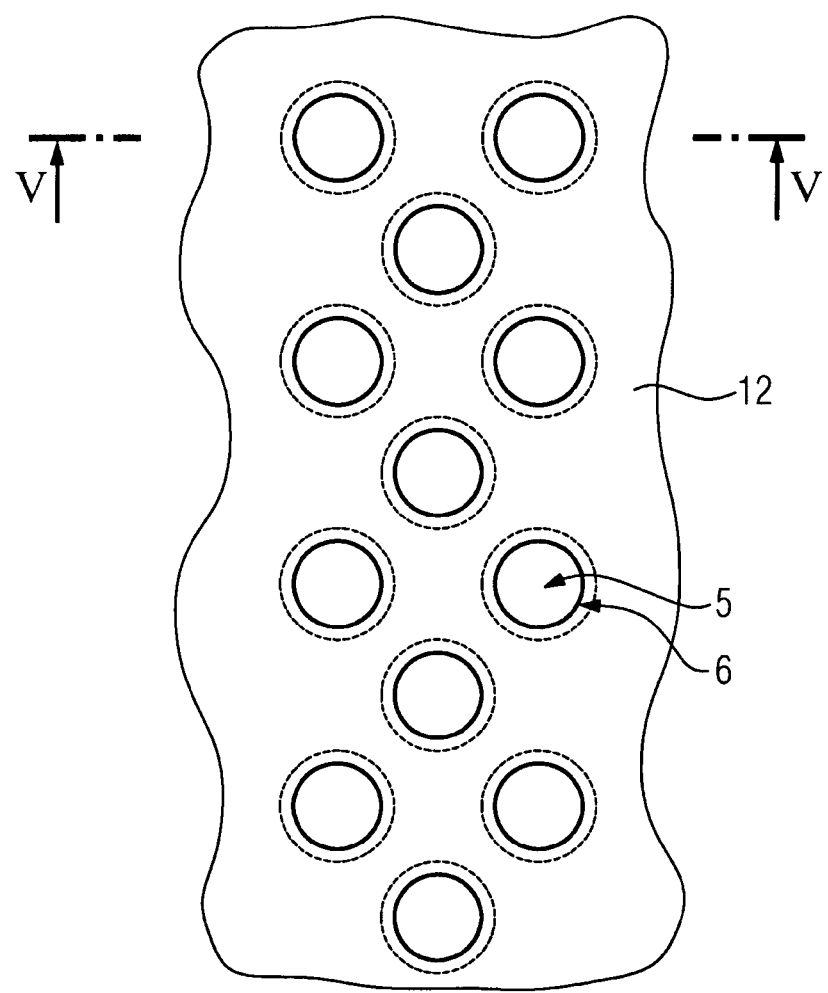

ARRANGEMENT AND METHOD FOR ELECTROCHEMICALLY MEASURING BIOCHEMICAL REACTIONS AND METHOD FOR PRODUCING THE ARRANGEMENT

CROSS REFERENCE TO RELATED APPLICATIONS

This application is based on and hereby claims priority to International Application No. PCT/EP2010/050842 filed on Jan. 26, 2010 and German Application Nos. 10 2009 007 387.6 filed on Feb. 4, 2009 and 10 2009 043 228.0 filed Sep. 28, 2009, the contents of which are hereby incorporated by reference.

BACKGROUND

The invention relates to a device for electrochemically measuring biochemical reactions, a method for producing the device and a method for electrochemically measuring biochemical reactions with the aforementioned device.

Electrochemical biosensors are used for a range of applications in biosensor technology, for example to detect viruses or antibodies or in DNA analysis. A range of detection reactions require particular temperature conditions and need to be subjected to particular temperature cycles. The electrochemical biosensors therefore need to be contacted not only electrically and fluidically, but also thermally. The electrochemical sensors generally comprise metal surfaces, which are coated or uncoated and which must be stable in the solutions to be analyzed. The sensors are arranged in array form on a base plate, in order to be able to carry out parallel measurements and for analyses of a plurality of individual components simultaneously.

When a sensor array is being used, each sensor spot or electrochemical sensor must be coated with a different recognition molecule. The specific coating may be carried out by lithographic methods or by spotting. Lithographic methods are very expensive and elaborate, since lithographic masks need to be prepared for each application and the chemical reactions for the coating comprise a series of steps.

Specific coating of the sensors by spotting with solutions which contain the recognition molecules to be applied, including binding groups, is simpler and more economical. When gold electrodes are used, binding groups may comprise thiol compounds which lead to directional binding of the recognition molecules on the gold surface. The electrodes may alternatively be formed of platinum, platinum being chemically very stable in a range of solutions, although during electrochemical measurements it may lead to a potential drift in the solutions being used.

The electrodes may be arranged mechanically stably on a base plate made of glass, silicon or plastic. In this case, the metal electrodes are applied onto the base plate by thin or thick film technology and electrically contacted via webs. In the case of silicon base plates, the measurement and evaluation electronics may be contained on the base plate in the form of an integrated circuit. Silicon is very expensive, however, and the production of integrated circuits on silicon is likewise expensive and elaborate. As an alternative, the base plate may be formed of printed circuit boards (PCB). The production of these is particularly straightforward and economical. Electrical leads and contacts are formed in the manner of copper tracks on the printed circuit board and electrically insulated from the environment by a varnish. The electrodes may be formed by coating the copper e.g. with gold, when using interlayers, and uncovered by the varnish layer.

By spotting liquids with different recognition molecules onto different electrodes of an array, the electrodes can be prepared for the specific detection of different biomolecules. For each electrode, a drop of a solution of a particular recognition molecule is spotted and the recognition molecules bind to the electrode. The solvent may be removed, for example by evaporation. During the spotting, however, it is necessary to prevent the spotting solution of one electrode from spreading over the surface of the base plate so that it comes into contact with a second electrode. Spreading can lead to unintended coating of a neighboring electrode, which will then not be specifically coated with recognition molecules and will not allow specific detection. In order to prevent the spotting solution from spreading, it is possible to use hydrophobic coatings of the base plate around the electrodes. This method is elaborate, not very reliable and works only when a small amount of solution is spotted.

Alternatively, it is possible to provide indentations in which the electrodes are embedded as a base surface of the indentation. In order to provide the indentations, for example, plastic rings may be fastened around the electrodes on the base plate or structured films, having recesses at the positions of the electrodes, may be applied or adhesively bonded onto the base plate. Elevations from the surface plane of the base plate are thereby formed, which act as a coating aid. However, these coating aids may, in the event of a fluid flow over the sensors, lead to formation and fixing of air bubbles which can interfere with an electrochemical measurement and which lead to false measurement results.

Fluidic contacting of the electrochemical biosensors is carried out by fitting a flow cell which is mechanically connected to the biosensor. The flow cell has an inlet channel and an outlet channel. Liquids to be studied can thus be pumped through the flow cell, i.e. flow over the sensor array on the base plate, and in the event of specific binding of biomolecules to individual sensors of the sensor array the binding events are measured by electrochemical signals. Fluidic contacting is in this case carried out from the base plate side on which the sensor array is arranged. Thermal contacting is carried out from the side of the base plate which lies opposite the base plate side with the sensor array.

Fitting a flow cell on the base plate with the biosensors and sealing with the aid of sealing rings often leads to problems in handling and to sealing problems. Arrangements composed of biosensors on a base plate and a fitted flow cell are generally constructed in a very complicated way, with a range of individual parts which are elaborate to manufacture. In particular, microcavities produced by milling with small structure sizes, which are often used in flow cells, are elaborate to produce.

SUMMARY

It is one possible object to provide an arrangement, and a method for electrochemically measuring biochemical reactions with the arrangement, which allow measurements without increased outlay, wherein the arrangement is to be produced fluid-tightly and allows reliably specific studies, with thermal control from the rear side of the arrangement. In particular, it is a potential object to ensure simple handling, to allow simple and inexpensive manufacture of the arrangement with the fewest possible parts, but nevertheless to provide a leaktight functional biosensor.

It is another potential object to provide a method for producing the arrangement, which prevents liquids from spreading when the electrodes are being coated and ensures laminar flow during use of the arrangement, owing to the planar surfaces without high elevations on the surface of the arrangement.

The aforementioned object is achieved in relation to the arrangement for electrochemically measuring biochemical reactions by the features of claim 1, in relation to the method for measuring with the arrangement by the features of claim 9, and in relation to the method for producing the arrangement by the features of claim 10.

The inventor proposes a device for electrochemically measuring biochemical reactions, which device comprises a base plate and a sensor array having at least two sensors which are formed on a first surface of the base plate and have active surfaces for detection of the biochemical reactions. The arrangement furthermore comprises a coating of the first surface of the base plate, a sealing film having at least one recess through which, in mechanical combination with the base plate and/or the coating of the base plate, a flow cell is formed over the sensor array, and at least one inlet channel and one outlet channel of the flow cell, which are formed in the manner of continuous openings in the base plate. The active surfaces of the sensors are at least partially or fully free of the coating, and regions of the base plate adjacent to the sensors are covered by the coating.

The use of a sealing film instead of a sealing ring, as is the case in the related art, allows a simple structure and simple handling when assembling the arrangement. Slipping of a sealing ring is prevented, and more reliable sealing of the flow cell is thus made possible.

The flow cell over the sensor array may be formed by the base plate and/or the coating of the base plate and by the sealing film in combination with a cover plate which is arranged on the sealing film, opposite to the first surface of the base plate. Via the cover plate, it is possible to exert a force on the sealing film which leads to compression of the film. Particularly good sealing of the flow cell is thereby achieved.

The active surfaces of the sensors and the coating of the base plate are spaced apart from one another so that trenches are formed around the sensors.

The trenches form a coating aid which, when spotting the specific recognition molecules, ensures that the spotted liquid of a spot does not spread simultaneously over a plurality of electrodes. The trenches fix a spotted drop on its edges and "hold" it over the spotted electrode. Liquid of the drop is sucked into the trenches by capillary forces, and the surface tension of the drop prevents further spreading over the surface outside the region of the spotted electrode. The solvent of the drop can evaporate, and the recognition molecules bind to the electrode.

The spacing of the active surfaces of the sensors from the coating of the base plate may have a value in the range of millimeters or micrometers, in particular a value in the vicinity of 50 µm. The electrodes may be formed in the manner of interdigital electrodes with finger-shaped webs, in which case the width of a web may lie in the vicinity of 100 µm and the total electrode diameter of an electrode may lie in the vicinity of 500 µm.

The trenches around the sensors may be formed fully continuously as far as the base plate and have a width and a depth with a value in the range of millimeters or micrometers, in particular a depth value in the vicinity of 40 µm and a width value in the vicinity of 50 µm. In this size range, capillary forces which can fix a drop act in the trenches.

The active surface of the sensors may be formed substantially in a common plane with at least one surface of the coating. Flow of liquid over the surface of the base plate with the sensor array, or the surface of the coating and sensors, leads to a flat surface, substantially formed in a common plane, of laminar flows. These flows improve the measurement accuracy of the sensors and prevent or avoid bubble formation and fixing of bubbles over the sensors on the surface.

As an alternative to forming trenches, edge regions of the active surfaces of the sensors may be coated with the coating. In this case, the different hydrophilic effects of metal surfaces and a coating can be utilized in order to fix liquid over the electrodes. A slight elevation in the micrometer range due to the coating over the electrodes can, with a rounded shape, permit laminar flow over the electrodes and prevent fixing of bubbles over the electrodes.

The sealing film may be a self-adhesive film, in particular a self-adhesive film with a double-sided coating of the film with an adhesive layer. This allows particularly simple fixing of the film on the base plate and prevents the sealing film from slipping when the flow cell is being assembled.

The inventor also proposes a method for electrochemically measuring biochemical reactions with the arrangement described above, which a method comprises the steps of introducing the sealing film, with a cover plate applied, into a holder which compresses the sealing film so that a seal of the flow cell is formed between the cover plate and the base plate. Needle-shaped inlet and outlet channels of the holder may be placed in the openings of the base plate.

Compression of the sealing film achieves reliable sealing of the flow cell. Positioning the inlet and outlet channels through the base plate makes the front side of the base plate fully accessible for the cover plate. Accurate alignment of the cover plate can be obviated, since the inlet and outlet channels cannot interfere. The entire front side may be covered by the cover plate, so that the entire sealing film is compressed.

The method for producing the arrangement described above comprises application of liquid onto the active surfaces of the sensors so that the coating of the first surface of the base plate is substantially not wetted. The active surface of the sensors comprises the molecules for binding and/or detecting biomolecules. The molecules for binding and/or detecting biomolecules can bind on the active surfaces of the sensors. Since the coating is not wetted, the liquid cannot spread over a plurality of sensors and specific functionalization of individual sensors is ensured.

The method for electrochemically measuring biochemical reactions and the method for producing the arrangement for electrochemically measuring biochemical reactions offer the aforementioned advantages associated with the arrangement for electrochemically measuring biochemical reactions.

BRIEF DESCRIPTION OF THE DRAWINGS

These and other objects and advantages of the present invention will become more apparent and more readily appreciated from the following description of the preferred embodiments, taken in conjunction with the accompanying drawings of which:

FIG. 1 shows a sectional representation of the proposed arrangement for electrochemically measuring biochemical reactions with a base plate and a sealing film, FIG. 2 shows a plan view of the arrangement shown in FIG. 1 with electrodes and terminals, FIG. 3 shows an enlarged view of a sectional representation of the sensor array according to a first exemplary embodiment with trenches, FIG. 4 shows a plan view of the sensor array of the first exemplary embodiment as shown in FIG. 3, FIG. 5 shows an enlarged view of a sectional representation of the sensor array according to a second exemplary embodiment with a coating overlapping the sensitive electrode surfaces, and FIG. 6 shows a plan view of the sensor array of the second exemplary embodiment as shown in FIG. 5.

DETAILED DESCRIPTION OF THE PREFERRED EMBODIMENT

Reference will now be made in detail to the preferred embodiments of the present invention, examples of which are illustrated in the accompanying drawings, wherein like reference numerals refer to like elements throughout.

FIG. 1 shows a sectional representation of the proposed arrangement with a base plate 1 and a sealing film 2. A cover plate 3 can be arranged on the sealing film 2, so that a flow cell is formed. FIG. 2 represents a plan view of the arrangement shown in FIG. 1, although for better clarity the cover plate 3 is not shown. Formed on the base plate 1, there is a sensor array 4 which comprises active surfaces of sensors 5 at regular spacings, arranged in array form. A reference electrode RE 8 is formed in the manner of a web that is located centrally between the working electrodes WE 6. A back electrode GE 7 spatially encloses the array of working electrodes 6, the back electrode 7 formed of two comb structures pointing toward each other. The resulting three electrode arrangements for electrochemical measurement give particularly reliable measurement results owing to the decoupling of the current flow and the voltage measurement. The electrodes 6, 7, 8 are respectively connected via electrical connections (not shown) on the base plate 1 to electrical terminals 9, via which the measurement signals can be acquired by an external reading unit. The electrical connections (not shown) are covered by a protective varnish 12 that electrically insulates the connections from liquid which may flow over the sensor array 4.

The base plate 1 is configured in the form of a printed circuit board. In general, the base plate is formed of PVC or a composite fiber material, and the electrical connections and electrical terminals 9 are produced from a copper layer, for example by etching two-dimensional structures. The electrodes 6, 7, 8 are likewise made from the copper layer, and they are additionally coated for example with gold. The reference electrode 8 may also be made by applying an Ag/AgCl paste. For better adhesion, bonding layers for example of nickel are generally arranged between the copper layer and the e.g. gold layer or Ag/AgCl paste.

Respectively separated spatially from the sensor array 4, two continuous bores are formed in the base plate 1. The bores are used as an inlet channel and an outlet channel 10. The sensor array 4 is arranged centrally on the surface of the base plate 1 between the bores.

A sealing film 2 is arranged on the side comprising the sensor array 4 and the electrical terminals 9 on the base plate 1. It may be placed on or adhesively bonded flat as a self-adhesive film onto the surface of the base plate 1. A recess 11 in the sealing film 2 encloses the inlet and outlet channels 10 and the sensor array 4 in the plan view of FIG. 2. The inlet and outlet channels 10, and the sensor array 4, are therefore not covered by the sealing film 2.

As shown in FIG. 1, a cover plate 3 may be applied onto the sealing film 2, in which case a sealing film 2 formed as double-sided adhesive tape allows adhesive bonding of the cover plate 3. As an alternative or in addition, fastening of the cover plate 3 on the sealing film 2 is also possible, for example by clamping devices. The recess 11 in the sealing film 2 forms, in combination with the inlet and outlet channels 10, a flow cell which is bounded by the base plate 1 with the sensor array 4 and by the sealing film 2 and the cover plate 3. When a force is exerted on the sealing film 2 via the cover plate 3, for example by a clamping device, the sealing film 2 can be slightly compressed and a fluid-tight flow cell can be produced. Fluid, for example the liquid to be analyzed with the biomolecules to be studied, can be supplied and discharged via the inlet and outlet channels 10, and flow over the sensor array 4. Electrochemical detection of the biomolecules is thus possible via the active surfaces of the sensors 5, which can be coated with specific recognition molecules or capture molecules, and measurement signals can be acquired and evaluated via the electrical terminals 9 by an external measurement and evaluation unit (not shown).

FIGS. 3 and 4 show a first exemplary embodiment of the arrangement with trenches 13 in a varnish layer 12 of the base plate 1. FIG. 3 shows a sectional representation along a section line 14 through the base plate 1 in the region of the sensor array 4. FIG. 4 shows a plan view of the sensor array 4 arranged on the base plate 1. The sensor array 4 includes eight working electrodes 6, in particular circular electrodes, which are arranged in two parallel rows each comprising four working electrodes 6. Centrally between the two rows, a finger-shaped reference electrode 8 is arranged parallel to the rows. The sensor array 4 is spatially enclosed by a back electrode 7 in the plane of the drawing. The back electrode 7 is constructed from two comb-shaped structures, which face each other with their comb fingers. On one side, the two comb-shaped structures are connected to establish contact.

As represented in FIG. 3, the active surfaces 5 of the electrodes 6, 7, 8 are arranged as e.g. a gold layer on the base plate 1. For the sake of simplicity, the electrical connections between the electrodes 6, 7, 8 and the electrical terminals 9, which are arranged on the base plate 1, are not represented. Regions of the base plate 1 which are not covered by active surfaces 5 of the electrodes 6, 7, 8 and by electrical terminals 9 are coated with a varnish 12. The varnish 12 is applied as a coating on the base plate 1 directly or indirectly, i.e. on the electrical connections.

Trenches 13 are formed between the active surfaces 5 of the electrodes 6, 7, 8 and the varnish layer 12. This means that the varnish layer 12 and the active surfaces 5 of the electrodes 6, 7, 8 are spatially separated from one another. The trenches 13 typically have a width in the vicinity of 50 μm and a depth in the vicinity of 40 μm. When the active surfaces 5 are coated, for example by spotting specific capture molecules contained in solution, the trenches 13 act as a coating aid. The liquid of a drop of solution on an active surface 5 is drawn into the trenches 13 by capillary forces and fixed over an active surface 5 by the surface tension. This prevents a drop on a first active surface 5 of a sensor 6 from spreading over a second active surface 5' of a neighboring sensor 6'. Specific coating of sensors 6, 6' with different capture molecules or recognition molecules is therefore possible. The solvent can evaporate, and specifically coated sensors 6, 6' or working electrodes of the sensor array 4 are obtained.

The trenches 13 may be formed continuously as far as the base plate 1. In general, however, at least the electrical connections between the electrodes 6, 7, 8 and the electrical terminals 9 are fully covered with varnish 12. In this case there may be a very thin varnish layer on the bottom of a trench 13, in particular with a thickness in the range of only a few micrometers, which is formed substantially thinner than the varnish layer 12 on the base plate 1 outside the trenches 13.

FIGS. 5 and 6 show an alternative second exemplary embodiment of the arrangement with a varnish layer 12 on the base plate 1 without trenches 13. FIG. 5 shows a sectional representation along a section line 14 through the base plate 1 in the region of the sensor array 4. FIG. 6 shows a plan view of the sensor array 4 arranged on the base plate 1. The sensor array 4 may be constructed in a similar way to the sensor array 4 of FIG. 4. As an alternative, FIG. 6 represents a sensor array 4 without a reference electrode 8 and back electrode 7. The sensor array 4 is formed of 12 working electrodes 6, which are arranged in three mutually offset rows on the base plate 1. The electrodes 6 are connected in a similar way to the first exemplary embodiment by connections (not shown) on the base plate 1 to electrical terminals 9.

The base plate 1 is coated with a varnish 12. The varnish 12 covers the electrodes 6 only in an edge region. The surfaces not covered by the varnish 12 form the active surfaces of a sensor 5. When the active surfaces 5 are being coated with specific capture molecules, for example by spotting, the varnish layer 12 acts as a coating aid. The varnish 12 forms a kind of well with the active surface of a sensor 5 as the bottom. The metal surface of the sensor 6 may have a greater affinity for the liquid than the varnish 12 does. A drop of the solution of specific capture molecules is prevented by the varnish 12 from spreading over regions outside an active surface 5 of a sensor 6.

The arrangement for electrochemically measuring biochemical reactions can be manufactured by a standard process for the production of printed circuit boards. The substrate of the base plate 1 is a plastic, which is flexible or rigid, and is formed for example of hard epoxy resin glass fabric. The sensor array 4 is initially produced in the form of conductive copper tracks, which are then electrolytically coated with gold so that they are suitable for electrochemical measurements. In order to produce indentations over or around the sensors 6, 7, 8 as a coating aid, as provided for example by trenches 13, a solder resist is applied and structured. For example, a 2-component epoxy resin resist may be used as the material, as is customary with the printed circuit boards. Since the base plate 1 is formed of a plastic, holes can be drilled in the circuit board by standard methods and can be used as an inlet channel and an outlet channel 10 for a flow cell. The two holes are then arranged so that they lie on opposite sides of the sensor array 4.

A sealing film 2, formed of, for example a silicone mat or a double-sided adhesive tape, is shaped so that the space over the electrodes 6, 7, 8 and the holes 10 remains free inside the sealing film 2. A cover plate 3, which need not necessarily be structured, is then placed on top. A simple small plastic plate may be used as the cover plate 3. This simple layer arrangement, formed of a printed circuit board 1, a sealing film 2 and a cover plate 3, is then put into a holder which places needles below the base plate 1 so that these end exactly in the holes 10. If a silicone mat is used as the sealing film 2, the holder needs to mechanically compress the layer arrangement so that fluid-tightness is ensured.

2-component epoxy resin resist is sufficiently biocompatible for many applications. The particular embodiment in which the photoresist 12 does not extend onto the electrodes 6, 7, 8 or only covers them in the edge region, for example flatly, provides a coating aid which allows particularly robust fluidics in subsequent use. The formation and fixing of gas bubbles over the active surfaces of the sensors 5 is thus prevented. A particularly simple embodiment of a flow cell is possible by virtue of the bores 10 in the printed circuit board or base plate 1.

The flow cell is formed by simple hollow needles in the holding apparatus in combination with the base plate 1, the sealing film 2 and the cover plate 3.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

The invention claimed is:

1. A device for electrochemically measuring biochemical reactions, comprising:
   a base plate;
   a sensor array having at least two sensors formed on a first surface of the base plate, each sensor having an active surface for detection of the biochemical reactions;
   a coating on the first surface of the base plate, the active surfaces of the sensors being at least partially or fully free of the coating and regions of the base plate adjacent to the sensors being covered by the coating; and
   a sealing film having at least one recess through which, in mechanical combination with the base plate and/or the coating on the base plate, a flow cell is formed over the sensor array,
   the flow cell having at least one inlet/outlet channel formed as a continuous opening in the base plate, the at least one inlet/outlet channel corresponding to the at least one recess in the sealing film,
   wherein the active surfaces of the sensors and the coating on the base plate are spaced apart from one another so that trenches are formed around the sensors.

2. The device as claimed in claim 1, wherein the flow cell is formed by the base plate and/or the coating on the base plate and by the sealing film in combination with a cover plate that is arranged on the sealing film opposite to the first surface of the base plate.

3. The device as claimed in claim 1, wherein a spacing of the active surfaces of the sensors from the coating on the base plate has a value in the range of millimeters or micrometers.

4. The device as claimed in claim 3, wherein the spacing of the active surfaces of the sensors from the coating on the base plate has a value of approximately 50 µm.

5. The device as claimed in claim 1, wherein the trenches around the sensors are formed fully continuously with respect to the base plate and have a depth with a value in the range of millimeters or micrometers.

6. The device as claimed in claim 5, wherein the trenches have a depth of approximately 40 µm.

7. The device as claimed in claim 1, wherein the active surfaces of the sensors are formed essentially in a common plane with at least one surface of the coating.

8. The device as claimed in claim 1, wherein edge regions of the active surfaces of the sensors are coated with the coating.

9. A device for electrochemically measuring biochemical reactions, comprising:
   a base plate;
   a sensor array having at least two sensors formed on a first surface of the base plate, each sensor having an active surface for detection of the biochemical reactions;
   a coating on the first surface of the base plate, the active surfaces of the sensors being at least partially or fully free of the coating and regions of the base plate adjacent to the sensors being covered by the coating; and
   a sealing film having at least one recess through which, in mechanical combination with the base plate and/or the coating on the base plate, a flow cell is formed over the sensor array, the flow cell having at least one inlet/outlet channel formed as a continuous opening in the base plate, the at least one inlet/outlet channel corresponding to the at least one recess in the sealing film, wherein the sealing film is a self-adhesive film.

10. The device as claimed in claim 9, wherein the sealing film is a self-adhesive film with a double-sided coating of the film with an adhesive layer.

11. The device as claimed in claim 9, wherein the flow cell is formed by the base plate and/or the coating on the base plate and by the sealing film in combination with a cover plate that is arranged on the sealing film opposite to the first surface of the base plate.

12. The device as claimed in claim 9, wherein a spacing of the active surfaces of the sensors from the coating on the base plate has a value in the range of millimeters or micrometers.

13. The device as claimed in claim 9, wherein the active surfaces of the sensors are formed essentially in a common plane with at least one surface of the coating.

14. The device as claimed in claim 9, wherein edge regions of the active surfaces of the sensors are coated with the coating.

15. A device for electrochemically measuring biochemical reactions, comprising:
 a base plate;
 a sensor array having at least two sensors formed on a first surface of the base plate, each sensor having an active surface for detection of the biochemical reactions;
 a coating on the first surface of the base plate, the active surfaces of the sensors being at least partially or fully free of the coating and regions of the base plate adjacent to the sensors being covered by the coating; and
 a sealing film having at least one recess through which, in mechanical combination with the base plate and/or the coating on the base plate, a flow cell is formed over the sensor array, the sealing film being a self-adhesive film, the flow cell having at least one inlet channel and one outlet channel formed as continuous openings in the base plate.

16. The device as claimed in claim 15, wherein a spacing of the active surfaces of the sensors from the coating on the base plate has a value in the range of millimeters or micrometers.

17. A device for electrochemically measuring biochemical reactions, comprising:
 a base plate;
 a sensor array having at least two sensors formed on a first surface of the base plate, each sensor having an active surface for detection of the biochemical reactions;
 a coating on the first surface of the base plate, the active surfaces of the sensors being at least partially or fully free of the coating and regions of the base plate adjacent to the sensors being covered by the coating; and
 a sealing film having at least one recess through which, in mechanical combination with the base plate and/or the coating on the base plate, a flow cell is formed over the sensor array,
 the flow cell having at least one inlet channel and one outlet channel formed as continuous openings in the base plate, and
 the active surfaces of the sensors and the coating on the base plate are spaced apart from one another so that trenches are formed around the sensors.

18. The device as claimed in claim 17, wherein the trenches formed around the sensors that have a depth with a value in the range of millimeters or micrometers.

* * * * *